United States Patent [19]
Rains, III

[11] Patent Number: 5,693,065
[45] Date of Patent: Dec. 2, 1997

[54] FRONTAL SINUS STENT

[76] Inventor: B. Manrin Rains, III, 8750 Walnut Grove Rd., Cordova, Tenn. 38018

[21] Appl. No.: 673,158

[22] Filed: Jun. 25, 1996

[51] Int. Cl.⁶ .................................. A61M 29/00
[52] U.S. Cl. ........................... 606/196; 604/902
[58] Field of Search ..................... 606/196, 199, 606/159; 604/902, 35

[56] References Cited

U.S. PATENT DOCUMENTS 4,767,404  8/1988  Renton .
5,588,952  12/1996  Dandolu ........................... 604/902

Primary Examiner—Michael Buiz
Assistant Examiner—Kevin Truong

[57] ABSTRACT

A self-retaining stent made of medical-grade silicone rubber that comprises a tube extended into a bulb on one end of said tube, said bulb consisting of multiple, radially-disposed ribs separated by openings into the bulb that allow fluid from the frontal sinus to drain into the bulb and thence through the tube after that stent has been inserted endoscopically into the frontal sinus.

4 Claims, 3 Drawing Sheets

FRONTAL SINUS STENT

SUMMARY

I have invented a self-retaining stent made of medical-grade silicone rubber that comprises a tube extended into a bulb on one end of said tube, said bulb consisting of multiple, radially-disposed ribs separated by openings into the bulb that allow fluid from the frontal sinus to drain into the bulb and thence through the tube after that stent has been inserted endoscopically into the frontal sinus.

DETAILED DESCRIPTION

Figure 1:
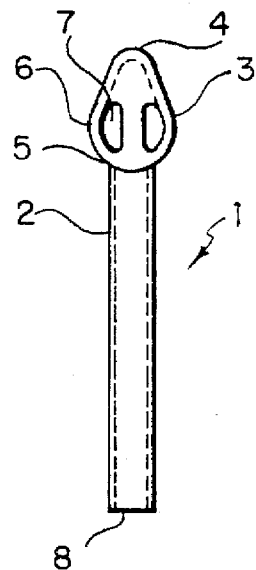
FIG. 1 is a two-dimensional view of my frontal sinus stent that shows the hollow interior of both the tube and bulb of my stent.

Restenosis of the frontal sinus drainage pathway has been a problem sinus surgeons have dealt with for many years. With the advent of endoscopic frontal sinus recess techniques, the success rate for endonasal sinus surgery has improved markedly. Although stenting is not always necessary, there are several situations where my frontal sinus stent helps to maintain patency of the frontal sinus drainage pathway during the healing process.

My stent is indicated for the frontal sinus drainage pathway in cases where there is significant denuded bone present after endoscopic frontal sinusotomy has been performed. My stent will help to prevent cicatricial stenosis. Also, in cases where extensive polypoid mucosa is present after the frontal recess is open, my stent has been found to help maintain patency of the frontal sinus drainage pathway.

In cases where purulent frontal sinusitis is present, the stent is helpful if used as an irrigation access point. And, in cases where the time-honored procedure of external frontal sinus trephination has been performed, my stent may be inserted and used as an irrigation port. It is possible to irrigate directly through the stent using a syringe, or to use a feeding tube through the lumen for endonasal frontal sinus irrigations.

Over the years, many materials from gold to rubber to silastic tubing have been used to stent the frontal sinus. Medical grade silicone rubber has been used for many years, particularly in tympanostomy tubes, and has minimal tissue reaction. However, those stents were inserted after external-type procedures, and none of those stents was self-retaining.

I have invented the first self-retaining frontal sinus stent made to be inserted endoscopically. My stent 1 may be made from any suitable material, but preferably is molded in one piece from medical-grade silicone rubber. My stent 1 is flexible and has an overall length of 1.90 inches from the tip of its bulb to its proximal end. The flexible tube 2 of my stent is circular and hollow, having an outer diameter of 0.157 inches and an inner diameter of 0.118 inches. The bulb 3 of my stent is hollow and egg-shaped, with the more pointed end at its tip 4 and the rounder end at its base 5 where it is molded onto the tube of the stent. The bulb of my stent has four flexible ribs 6 spaced equidistant around its periphery, and the space 7 between each adjacent two ribs is open. Each of those four ribs 6 is 0.080 inches wide and 0.05 inches thick. When fully extended, the outer surfaces of each pair of opposite ribs 6 are 0.305 inches apart. The wall of the bulb 3 is also 0.05 inches thick. The bulb 3 of my stent 1 is 0.47 inches from its tip 4 to its base 5, and the opening 7 between each adjacent two ribs 6 of the bulb is 0.181 inches long. Each opening 7 between adjacent ribs 6 allows fluid to enter into the hollow of the bulb 3 and flow through the bulb 3 into and through the tube 2, ultimately draining out of the proximal end 8 of the tube 2 of my stent.

Figure 2:
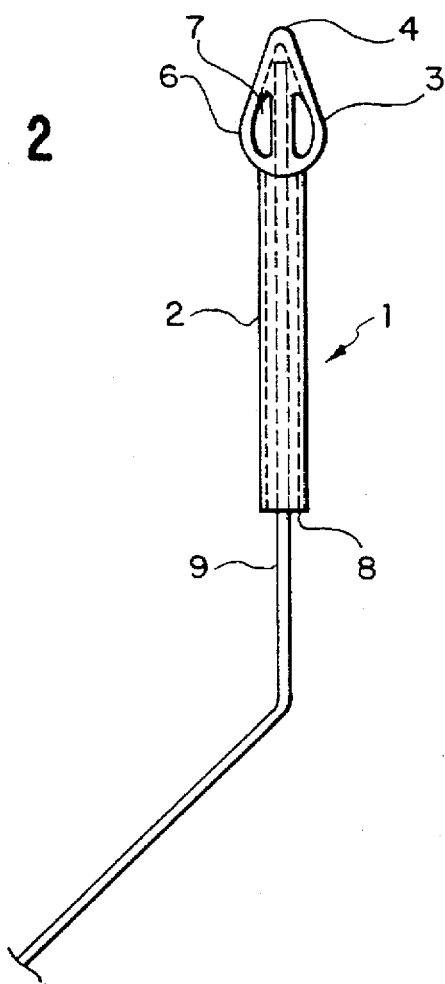
FIG. 2 is a two-dimensional view of my frontal sinus stent into which a rigid, suction tube has been inserted to collapse the ribs of the bulb to enable endoscopic insertion of the stent into the frontal sinus of a patient.
Figure 3:
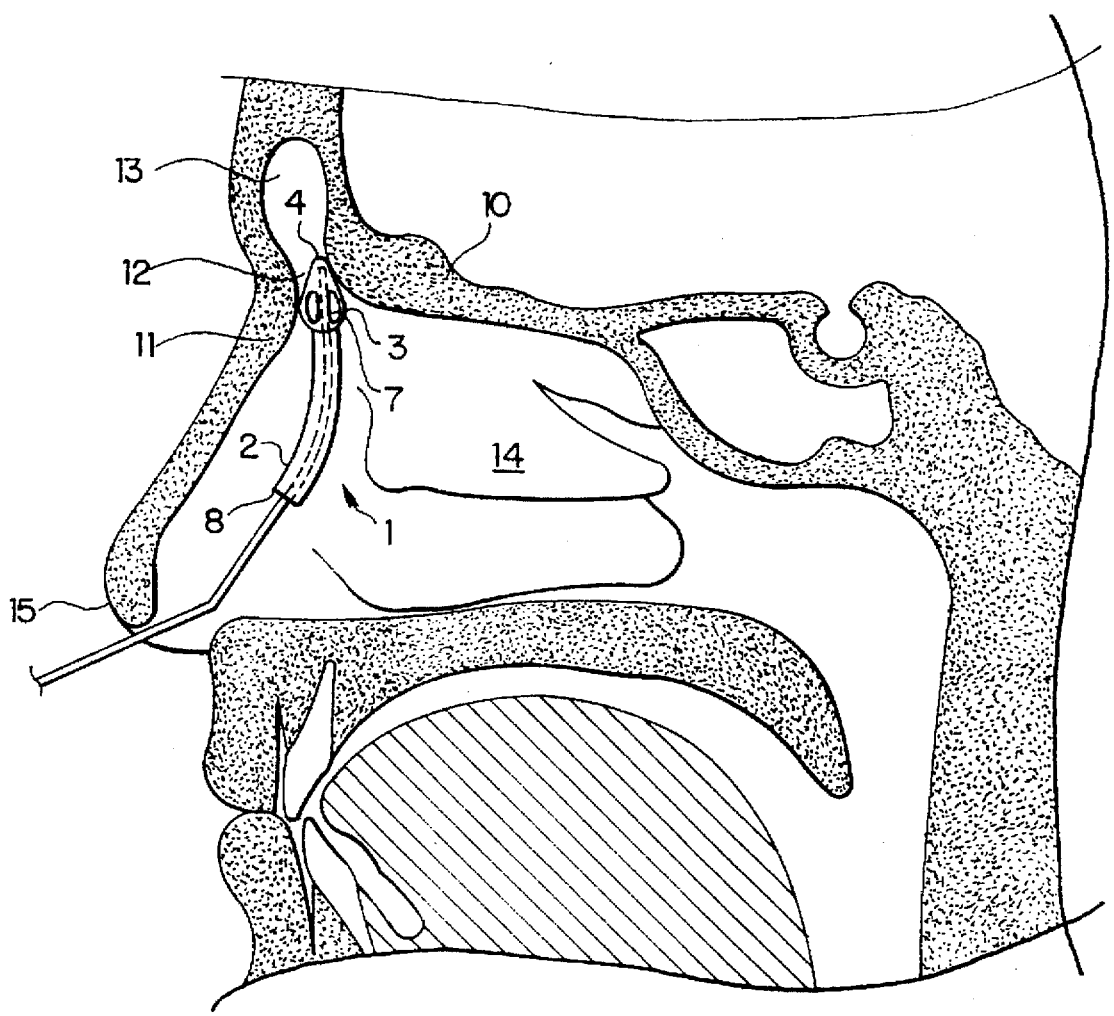
FIG. 3 is a two-dimensional view of my frontal sinus stent into which a rigid, suction tube has been inserted as shown in FIG. 2 that shows the stent being inserted into the frontal sinus of a patient.

If stenting the frontal sinus is indicated, my stent may be used in the following manner. Slide my frontal sinus stent over a 16-gauge up-curved frontal sinus suction tube 9 as shown in FIG. 2, or over a frontal ostia seeker, until the ribs 6 of its bulb 3 collapse. The suction tube 9 provides the added benefit of being able to remove blood in the field and offers improved visibility during this procedure. Next, insert the collapsed bulb 3 of the stent 1 through the newly opened frontal sinus drainage pathway 12 as shown in FIG. 3. The bulb 3 of the stent 1 is helped to collapse by the pressure provided by bone 10 or bone covered by mucous membrane 11 as it passes through the frontal sinus drainage pathway 12 as shown in FIG. 3.

Figure 4:
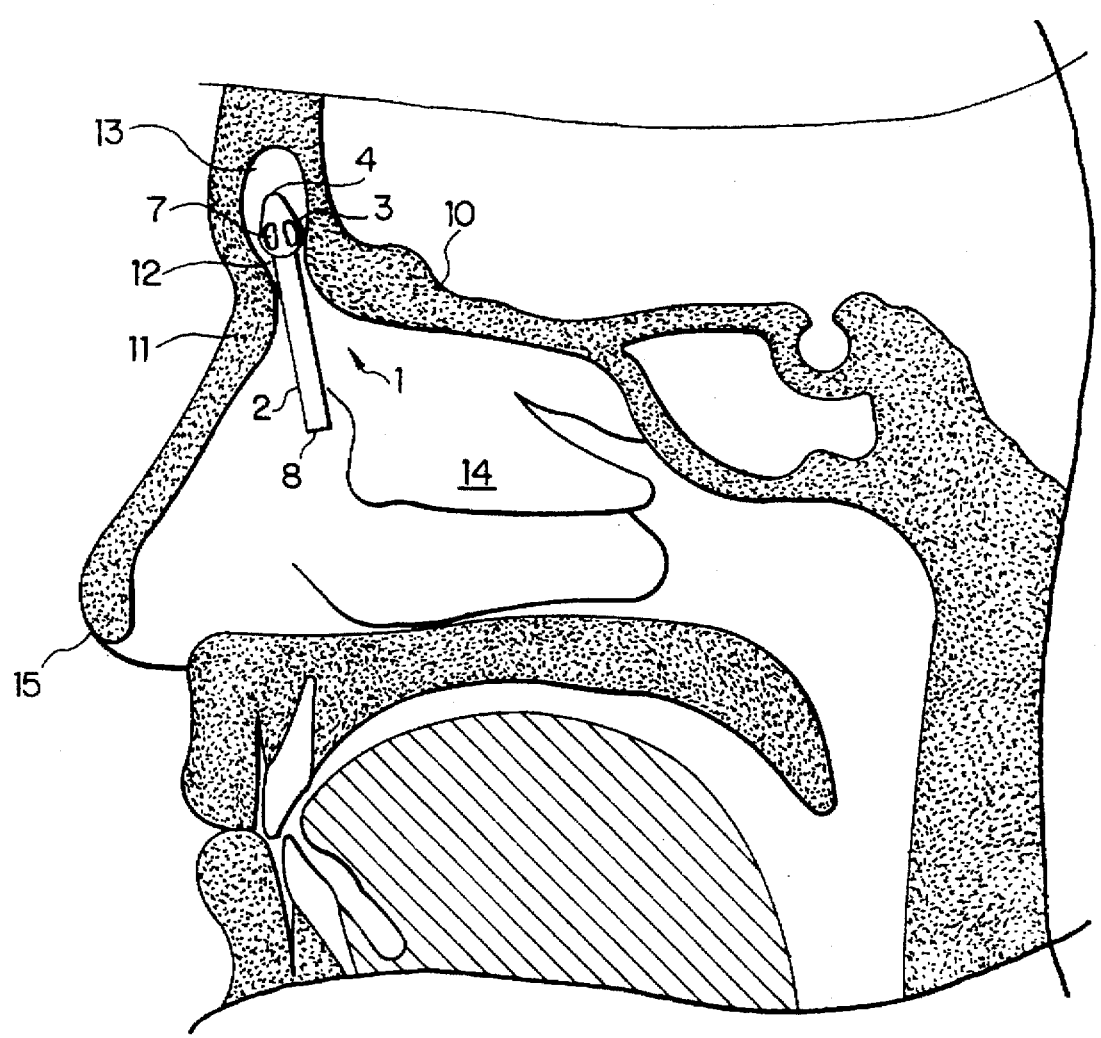
FIG. 4 is a two-dimensional view of my frontal sinus stent shown after insertion of the stent into the frontal sinus of a patient and withdrawal of the rigid suction tube from inside the tube and bulb of the stent.

After the bulb 3 of the stent 1 has been inserted past the frontal sinus drainage pathway 12 into the frontal sinus 13, the frontal sinus suction tube 9 or frontal ostia seeker may be removed while holding the proximal end 8 of my stent in place with the tip of an endoscope. When the suction tube 9 or ostia seeker is removed from the bulb 3 of the stent tube 2, the ribs 6 of the bulb 3 of the stent 1 extend back into their original radial shape and those extended ribs 6 retain the tube 2 of the stent 1 in place in the frontal sinus 13 as shown in FIG. 4.

If the proximal end 8 of the stent tube 2 extends past the inferior border of the middle turbinate 14, it may be trimmed with scissors. The stent 1 retains itself in place during the healing process, and may serve as an access tube for irrigation of the frontal sinus 13 during the healing process. After the stent is no longer needed, it may be removed easily in the surgeon's office by grasping the proximal end 8 of the stent 1 and pulling the stent out through the frontal sinus drainage pathway 12 and nose 15. During removal, the ribs 6 of the bulb 3 of the stent 1 will collapse from external pressure exerted by bone 10 or bone covered by mucous membrane 11 of the pathway. If needed, a topical anesthesia may be administered to the patient during this removal of the stent, which may be performed in the office of the surgeon.

Normal postoperative care for the endoscopic sinus surgery patient is well known, and usually consists of endoscopic examination of the patient on the first postoperative day, when mucous plugs and clots are removed. If any sinus packs have been inserted, these are removed at this time. The patient is examined every four to seven days for the first three weeks until the initial healing phase has resolved. Once the ethmoidectomy sites have healed and tissue edema is decreasing, the frontal sinus stent can be removed.

The patient is maintained on appropriate postoperative antibiotics. If there is marked polypoid mucosal disease, particularly with eosinophilia present in the polyps, then a course of oral steroids is undertaken. Topical steroids are usually begun after one to two weeks following the operation.

I have attempted to describe the best mode of making and using my frontal sinus stent, and I intend to protect that mode, and all equivalent modes, or other similar modes that are simply minor or immaterial variations from the spirit of my invention.

I claim:

1. A frontal sinus stent that comprises a flexible, resilient hollow bulb affixed to the wall of said flexible hollow tube at one of said two ends of said tube, said bulb including multiple resilient ribs separated by at least one opening into said hollow bulb between each pair of said ribs, at least one of said openings into said hollow bulb together with said tube providing a fluid conduit, said ribs extending sufficiently beyond the periphery of said tube to retain said stent in a frontal sinus.

2. A frontal sinus stent as described in claim 1 wherein the bulb and tube are molded together as one piece of flexible hollow material.

3. A frontal sinus stent as described in claim 1 wherein the bulb and tube are molded together as one piece from medical grade silicone rubber.

4. A frontal sinus stent as described in claim 1 wherein the bulb includes four ribs separated by four openings.

* * * * *